United States Patent
Yoo

(10) Patent No.: US 9,390,533 B2
(45) Date of Patent: Jul. 12, 2016

(54) METHOD AND APPARATUS FOR DISPLAYING AN ADDITIONAL INFORMATION RELATED TO MEASURED VALUE OF OBJECT

(71) Applicant: SAMSUNG MEDISON CO., LTD., Gangwon-Do (KR)

(72) Inventor: Jun-Sang Yoo, Gangwon-Do (KR)

(73) Assignee: SAMSUNG MEDISION CO., LTD., Hongcheon-Gun, Gangwon-Do (KR)

( * ) Notice: Subject to any disclaimer, the term of this patent is extended or adjusted under 35 U.S.C. 154(b) by 97 days.

(21) Appl. No.: 14/445,902

(22) Filed: Jul. 29, 2014

(65) Prior Publication Data

US 2015/0178969 A1    Jun. 25, 2015

(30) Foreign Application Priority Data

Dec. 19, 2013    (KR) .................. 10-2013-0159639

(51) Int. Cl.

| | |
|---|---|
| G06T 11/60 | (2006.01) |
| G06T 7/60 | (2006.01) |
| G06T 11/00 | (2006.01) |
| G06T 15/40 | (2011.01) |
| G09G 5/02 | (2006.01) |
| G09G 5/14 | (2006.01) |
| G06F 3/048 | (2013.01) |
| H04N 5/44 | (2011.01) |
| G06F 19/00 | (2011.01) |

(52) U.S. Cl.
CPC ............ *G06T 11/60* (2013.01); *G06F 19/3406* (2013.01); *G06T 7/60* (2013.01); *G06T 11/001* (2013.01); *G06T 2210/41* (2013.01)

(58) Field of Classification Search
CPC combination set(s) only.
See application file for complete search history.

(56) References Cited

U.S. PATENT DOCUMENTS

| | | | |
|---|---|---|---|
| 6,019,723 A | 2/2000 | Yamaura | |
| 2012/0065513 A1* | 3/2012 | Lee | G01S 7/52065 600/443 |
| 2012/0101383 A1 | 4/2012 | Hyun | |
| 2014/0164997 A1* | 6/2014 | Lee | G06F 3/04883 715/810 |
| 2014/0330120 A1* | 11/2014 | Shin | A61B 8/485 600/438 |
| 2015/0220240 A1* | 8/2015 | Tsukijishin | A61B 5/7445 348/77 |

FOREIGN PATENT DOCUMENTS

| | | |
|---|---|---|
| EP | 2444002 A1 | 4/2012 |
| KR | 10-0352053 B | 4/2003 |
| KR | 10-2012-0043642 A | 5/2012 |
| WO | 2009136332 A2 | 11/2009 |

\* cited by examiner

OTHER PUBLICATIONS

Extended European Search Report dated May 20, 2015 issued in European Patent Application No. 14167495.2.

*Primary Examiner* — Wesner Sajous
(74) *Attorney, Agent, or Firm* — McDermott Will & Emery LLP

(57) ABSTRACT

Provided is a method of displaying additional information related to a measured value of an object, which includes acquiring measurement item information of the object; acquiring at least one of a measurement point and a measurement direction for the object; determining a reference value for a measurement based on the acquired measurement item information; acquiring the measured value of the object based on the at least one of the measurement point and the measurement direction; and displaying additional information including the determined reference value and the acquired measured value.

17 Claims, 12 Drawing Sheets

METHOD AND APPARATUS FOR DISPLAYING AN ADDITIONAL INFORMATION RELATED TO MEASURED VALUE OF OBJECT

RELATED APPLICATIONS

This application claims the benefit of Korean Patent Application No. 10-2013-0159639, filed on Dec. 19, 2013, in the Korean Intellectual Property Office, the disclosure of which is incorporated herein in its entirety by reference.

BACKGROUND

1. Field

One or more embodiments of the present invention relate to a method and apparatus for displaying additional information related to a measured value of an object, and more particularly, to a method and apparatus for displaying an average value or an abnormal value contained in additional information related to a measured value of an object, together with the measured value.

2. Description of the Related Art

Examples of medical diagnostic equipment may include an ultrasound diagnosis device, an X-ray photographing apparatus, a computerized tomography (CT) apparatus, and a magnetic resonance imaging (MRI) device.

Among these, an ultrasound diagnosis device transmits ultrasound signals from a body surface of a target object toward a predetermined portion inside a body and uses information of ultrasound signals reflected from tissues in the body to obtain tomographic images of soft tissues or blood flow.

Such an ultrasound diagnosis device may display information regarding a target object in real-time. Furthermore, an ultrasound diagnosis device causes no radioactive exposure like X-rays, thus being highly safe. Therefore, ultrasound diagnosis devices have been widely used together with other types of imaging diagnosis devices, including X-ray diagnosis devices, CT scanners, MRI devices, nuclear medical diagnosis devices, etc.

One type of a radiographic imaging apparatus for medical diagnostics may be an X-ray photographing apparatus.

In general, X-rays are electromagnetic waves having a wavelength of 0.01 to 100 angstroms (Å) and can penetrate into an object. Thus, they may be commonly used in a wide range of applications such as medial devices that take images of the inside of a living body and non-destructive testing equipment for industrial use.

An X-ray photographing apparatus uses X-rays emitted by an X-ray tube (or X-ray source) to penetrate into an object, detects a difference in intensity of the X-rays from an X-ray detector, and identifies the internal structure of the object. Furthermore, the X-ray photographing apparatus is able to easily identify the internal structure of the object by using the principle that the amount of X-rays that penetrate the object varies depending on the density of the object and atomic number of an atom in the object. As the wavelength of an X-ray becomes shorter, permeability of X-rays increases, and a screen becomes brighter.

An X-ray photographing apparatus generally includes an X-ray source, an X-ray detector, and an image processor. The X-ray source irradiates an X-ray under predetermined X-ray irradiation conditions, and the X-ray detector acquires image data based on an X-ray that penetrates the object and transmits the image data to the image processor. The image processor then processes the image data to provide an image of the object to a display unit.

Another type of a radiographic imaging apparatus for medical diagnostics may be a CT system. Since the CT system is capable of providing a cross-sectional image of an object, the CT system may represent an inner structure (e.g., an organ such as a kidney, a lung, etc.) of the object without an overlap therebetween, compared to a general X-ray imaging apparatus.

The CT system may obtain a plurality of pieces of image data with a thickness of not more than 2 mm for several tens to several hundreds of times per second and then may process the plurality of pieces of image data, thereby providing a relatively accurate cross-sectional image of the object. In other words, the internal structure of the object may be generated as a two- or three-dimensional (2D or 3D) image by a plurality of 2D X-ray image data obtained around a single rotation axis.

Furthermore, MRI equipment may be used for medical diagnosis.

MRI is a technology that acquires an image of an object by measuring a difference between signals that are emitted from a tissue in an object by applying a radio frequency (RF) pulse that causes protons in the object to resonate and reconstructing the difference through a computer, wherein the object is placed inside a large magnet for producing a magnet field. An MRI system exhibits high resolution and high contrast over another imaging technique using ultrasound and is capable of providing images of deep organs and 3D information in real-time. The MRI system also involves no exposure to radiation and thus is harmless to a human body. Furthermore, the MRI system may create images in the axial plane, in the sagittal plane, and in the coronal plane without any change in a position of an object.

SUMMARY

One or more embodiments of the present invention include a method and apparatus for displaying additional information related to a measured value of an object.

Additional aspects will be set forth in part in the description which follows and, in part, will be apparent from the description, or may be learned by practice of the presented embodiments.

According to one or more embodiments of the present invention, a method of displaying additional information related to a measured value of an object includes: acquiring measurement item information of the object; acquiring at least one of a measurement point and a measurement direction for the object; determining a reference value for a measurement based on the acquired measurement item information; acquiring the measured value of the object based on the at least one of the measurement point and the measurement direction; and displaying additional information including the determined reference value and the acquired measured value. The measurement item information of the object includes profile information of the object and information about a measurement item determined according to a portion of the object to be measured.

The measurement point may include a measurement start point and a measurement end point, and the measurement end point may be designated by moving a predetermined pointer for designating the measurement point from the measurement start point in a predetermined direction.

The determining of the reference value based on the measurement item information may include determining an average value, an abnormal value, or a value of interest for diagnosis, related to the measurement item, based on the profile information of the object.

The measured value of the object may include a length, a perimeter, an angle, an area, or a volume, and the acquiring of the measured value of the object based on the at least one of the measurement point and the measurement direction may include acquiring a length of a straight line formed by moving the predetermined pointer from the measurement start point, a perimeter of a curve formed by moving the predetermined pointer from the measurement start point, an angle formed by a plurality of lines including the measurement start point, an area having a predetermined shape including the measurement start point, or a volume of a 3D region including the measurement start point.

The displaying of the additional information including the determined reference value and the acquired measured value may include allocating a predetermined color to the reference value and displaying the additional information including the reference value having the predetermined color and the measured value at a predetermined location on a medical image of the object.

The predetermined location may overlap a straight line formed between measurement start and end points.

The predetermined location may be adjacent to a straight line formed between the measurement start and end points, and the displaying of the additional information including the determined reference value and the acquired measured value may include: allocating a predetermined color to the reference value; generating a color bar including the color allocated to the reference value; and displaying the generated color bar as the additional information.

The acquiring of the measured value of the object based on the at least one of the measurement point and the measurement direction may include acquiring a measured value in real-time each time the predetermined pointer is moved from the measurement start point in a predetermined direction. The displaying of the additional information including the determined reference value and the acquired measured value may include: allocating a predetermined color to the reference value; generating a color bar including the color allocated to the reference value; displaying the generated color bar; and displaying the measured value in color that corresponds to the measured value acquired in real-time among colors included in the color bar.

According to one or more embodiments of the present invention, an apparatus for displaying additional information related to a measured value of an object includes: an object information acquisition unit for acquiring measurement item information of the object; a measurement item information acquisition unit for acquiring at least one of a measurement point and a measurement direction for the object; a reference determination unit for determining a reference value for a measurement based on the acquired measurement item information; a measured value acquisition unit for acquiring the measured value of the object based on the at least one of the measurement point and the measurement direction; and a display unit for displaying additional information including the determined reference value and the acquired measured value. The measurement item information of the object includes profile information of the object and information about a measurement item determined according to a portion of the object to be measured.

The measurement point may include a measurement start point and a measurement end point, and the measurement end point may be designated by moving a predetermined pointer for designating the measurement point from the measurement start point in a predetermined direction.

The reference determination unit may determine an average value, an abnormal value, or a value of interest for diagnosis, related to the measurement item, based on the profile information of the object.

The measured value of the object may include a length, a perimeter, an angle, an area, or a volume, and the measured value acquisition unit may acquire a length of a straight line formed by moving the predetermined pointer from the measurement start point, a perimeter of a curve formed by moving the predetermined pointer from the measurement start point, an angle formed by a plurality of lines including the measurement start point, an area having a predetermined shape including the measurement start point, or a volume of a 3D region including the measurement start point.

The apparatus may further include a color allocation unit for allocating a predetermined color to the reference value, and the display unit may display the additional information including the reference value having the predetermined color and the measured value at a predetermined location on a medical image of the object.

The predetermined location may overlap a straight line formed between measurement start and end points.

The apparatus may further include a color allocation unit for allocating a predetermined color to the reference value and a color bar generator for generating a color bar including the color allocated to the reference value.

The display unit may display the generated color bar as the additional information, and the predetermined location may be adjacent to a straight line formed between the measurement start and end points.

The apparatus may further include a color allocation unit for allocating a predetermined color to the reference value and a color bar generator for generating a color bar including the color allocated to the reference value.

The measured value acquisition unit may acquire a measured value in real-time each time the predetermined pointer is moved from the measurement start point in a predetermined direction, and the display unit may display the generated color bar, and the measured value in color that corresponds to the measured value acquired in real-time among colors included in the color bar.

According to one or more embodiments of the present invention, a non-transitory computer-readable recording medium has recorded thereon a program for executing the above-described method on a computer.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
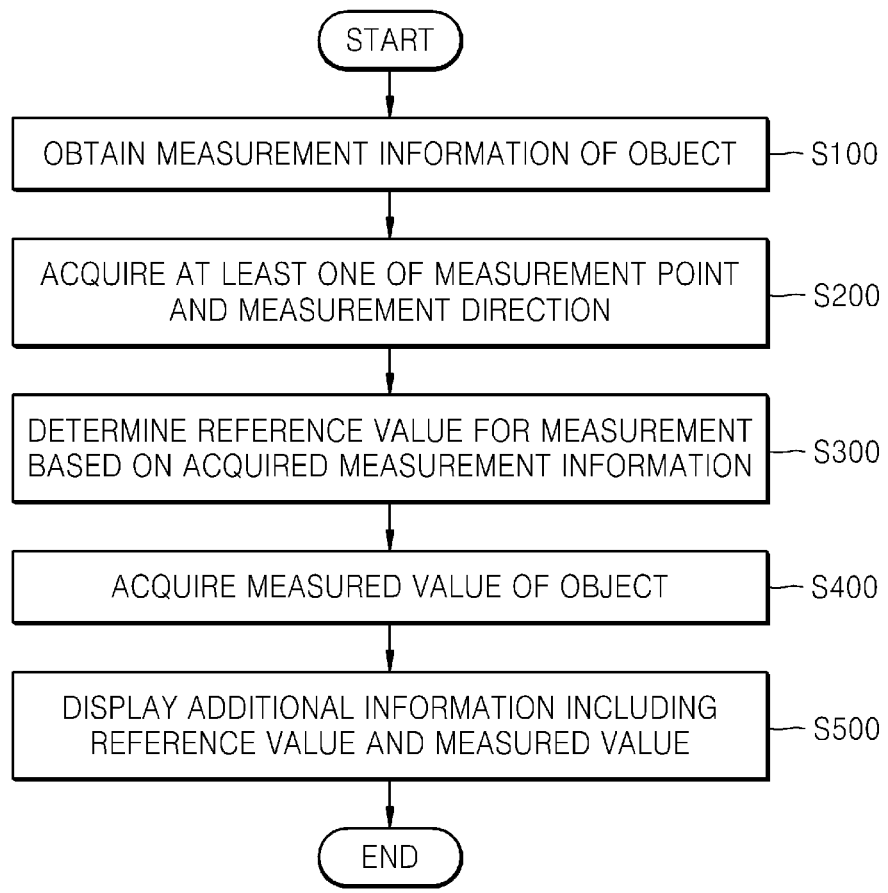
FIG. 1 is a flowchart of a method of displaying additional information related to a measured value of an object, according to an exemplary embodiment of the present invention.

Terms used herein will now be briefly described and then one or more embodiments of the present invention will be described in detail.

General terms widely used are selected while considering functions in one or more embodiments of the present invention for terms used herein, but the terms used herein may differ according to intentions of one of ordinary skill in the art, precedents, or emergence of new technologies. Also, in some cases, an applicant arbitrarily selects a term, and in this case, the meaning of the term will be described in detail herein. Accordingly, the terms shall be defined based on the meanings and details throughout the specification, rather than the simple names of the terms.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

In the present specification, a "medical image" may mean multi-dimensional data composed of discrete image elements (for example, pixels in a two-dimensional (2D) image and voxels in a three-dimensional (3D) image). For example, a medical image may include images of an object acquired by an X-ray, a CT, an MRI, an ultrasound wave, and other medical imaging systems. The object may refer to parts of a body. For example, the object may include organs such as the liver, the heart, the uterus, the brain, a breast, and the abdomen, or a fetus.

Furthermore, in the present specification, a "user" refers to a medical professional, such as a doctor, a nurse, a medical laboratory technologist, and a medical imaging expert, but is not limited thereto.

Exemplary embodiments will now be described more fully hereinafter with reference to the accompanying drawings so that they may be easily implemented by one of ordinary skill in the art. However, the present exemplary embodiments may have different forms and should not be construed as being limited to the descriptions set forth herein. Parts not related to the present invention are omitted for clarity of the description of the exemplary embodiments of the present invention. In the accompanying drawings, like reference numerals refer to like elements throughout. Expressions such as When a length and an area of an object is measured, a user needs to use a percentile table to determine whether a measured length or area falls in a normal range (or normal group) or an abnormal range (or abnormal group). Furthermore, according to a conventional technique, it may be difficult for a user to identify a difference between a measured value and a reference value for distinguishing a normal group from an abnormal group.

According to an embodiment of the present invention, by indicating additional information including a reference value related to a measured value of an object, a user may easily determine whether the measured value falls in a normal range (or normal group) or an abnormal range (abnormal group).

FIG. 1 is a flowchart of a method of displaying additional information related to a measured value of an object, according to an exemplary embodiment of the present invention.

The method according to the present embodiment includes obtaining measurement item information of an object (S100), acquiring at least one of a measurement point and a measurement direction for the object (S200), determining a reference value for a measurement based on the measurement item information of the object (S300), acquiring a measured value of the object based on at least one of the measurement point and the measurement direction (S400), and displaying additional information containing the determined reference value and the acquired measured value (S500).

The measurement item information of the object may include profile information of the object and information about measurement items that are determined according to a portion of the object to be measured. For example, the measurement item information of the object may include profile information of the object containing a gestational age (GA) as well as data for estimating a GA. For example, if a parameter such as a Crow-Rump Length (CRL) or Head Circumference (HC) is available, a GA may be estimated (predicted) based on the CRL or HC.

The measurement item information may also include portions of the object to be measured and measurement items predetermined for the portions of the object to be measured. The portions of the object to be measured may include the head, the heart, the abdomen, arms, and legs of a fetus or adult.

The measurement items may be set automatically or manually. For example, high priorities may be pre-assigned to measurement items having high frequencies of measurement for a portion to be measured, and the measurement items may be automatically set according to the pre-assigned priorities.

The measurement items may include biometric information of a fetus such as a CRL, a Bi-Parietal Diameter (BPD), an Abdominal Circumference (AC), a Head Circumference (HC), cerebellum (CIA, or a Femur Length (FL). The measurement items may also include items for checking a status of fetal growth, such as propagation velocity (Vp), Occipito-Frontal Diameter (OFD), Fetal Trunk Area (FTA), and Expected Fetal weight. The measurement items may also include a Nuchal translucency (NT) length (or thickness) and Intracranial Translucency (IT) for determining malformations such as fetal chromosome abnormalities, but are not limited thereto.

A reference value for a measurement according to an embodiment of the present invention may include a percentile rank or percentage corresponding to measurement item information. For example, if the object is a fetus, the reference value may include a percentile rank or percentage of a measurement average value, a value determined to be abnormal, or a value of interest for diagnosis at a GA of the fetus.

A reference value according to an embodiment of the present invention may be displayed as at least one of a dot, a line, a face, a number, and a letter.

In the operation of obtaining measurement item information of an object (S100), the measurement item information may be input from a user through an external input receiver (not shown). For example, the measurement item information such as profile information of the object containing a GA or information about portions of the object to be measured and measurement items may be acquired by the user through the external input receiver.

The operation of acquiring at least one of a measurement point and a measurement direction for the object (S200) may include receiving at least one of the measurement point and the measurement direction for the object from the user through the external input receiver.

The measurement point of the object may include a measurement start point and a measurement end point. The measurement end point may be designated by moving a predetermined pointer for designating the measurement point from the measurement start point in a predetermined direction. The predetermined pointer may be an indicator (or a cursor) having an arrow or finger shape. For example, the user may designate a measurement end point by first clicking a measurement start point with a cursor and then moving the cursor in a predetermined direction to click a point other than the measurement start point.

The operation of determining a reference value for a measurement based on the measurement item information of the object (S300) may include determining an average value, an abnormal value, and a value of interest for diagnosis for a measurement item, based on profile information of the object For example, a measurement average value, an abnormal value for distinguishing normality from abnormality, or a value of interest for diagnosis may be pre-stored in a predetermined storage device (not shown).

Furthermore, the measurement average value, the abnormal value, or the value of interest may be determined by statistical operations. For example, measurement data related to a plurality of objects may be acquired from a device that is able to make data communication according to a Picture Archiving and Communication System (PACS) or Digital Imaging and Communications in Medicine (DICOM) standard, and an average value, an abnormal value, or a value of interest for diagnosis for a measurement item may be determined based on the acquired measurement data by using a statistical method.

The operation of acquiring a measured value of the object based on at least one of the measurement point and the measurement direction (S400) may include measuring a portion of user's interest using a measurement end point that is determined by moving from a measurement start point along a measurement direction and acquiring the measured value of the object.

The measured value of the object may include a length, a perimeter, an angle, an area, or a volume. In other words, the operation S400 includes acquiring a length of a straight line formed by moving a predetermined pointer from a measurement start point, a perimeter of a curve formed by moving a predetermined pointer from a measurement start point, an angle formed by a plurality of lines including a measurement start point, an area having a predetermined shape including a measurement start point, or a volume of a 3D region including a measurement start point, as described below with reference to FIGS. 3A through 3D.

Referring back to FIG. 1, as described above, the method according to the present embodiment also includes displaying additional information containing the determined reference value and the acquired measured value (S500).

The operation of displaying additional information containing the determined reference value and the acquired measured value (S500) may include allocating a predetermined color to the determined reference value and displaying additional information including a reference value having the predetermined color and the acquired measured value at a predetermined location on a medical image of the object. As described above, a medical image according to an embodiment of the present invention may include images of the object acquired by an X-ray, a CT, an MRI, and other medical imaging systems.

The predetermined location may overlap a straight line formed between measurement start and end points. For example, the additional information may be displayed in such a way as to overlap the straight line therebetween.

Alternatively, the predetermined location may be adjacent to the straight line formed between the measurement start and end points. In other words, the predetermined location may be on the left or right side of the straight line.

As another example, the operation S500 may include allocating a predetermined color to the determined reference value, generating a color bar including the predetermined color allocated to the reference value, and displaying the color bar as additional information. Although the reference value may be displayed as characters or numbers, a relative relationship between the measured value and the reference value may be represented by using a color allocated to the reference value. For example, by generating a color bar including the color allocated to the reference value as a gradation bar, etc., the user may quickly recognize the extent to which the measured value falls short of or exceeds the reference value.

The operation S400 may include acquiring a measured value in real-time each time a predetermined pointer is moved from a measurement start point in a predetermined direction. In other words, a portion of the object may be measured in real-time by moving the predetermined pointer.

Furthermore, the operation S500 may include allocating a predetermined color to the determined reference value, generating a color bar including the color allocated to the reference value, displaying the color bar, and displaying the measured value in color that corresponds to a measured value obtained in real-time among colors included in the color bar.

The operation S500 will be described in more detail below with reference to FIGS. 2A through 2E.

FIGS. 2A through 2E illustrate examples of displayed additional information related to a measured value of an object according to an exemplary embodiment of the present invention.

Figure 2A:
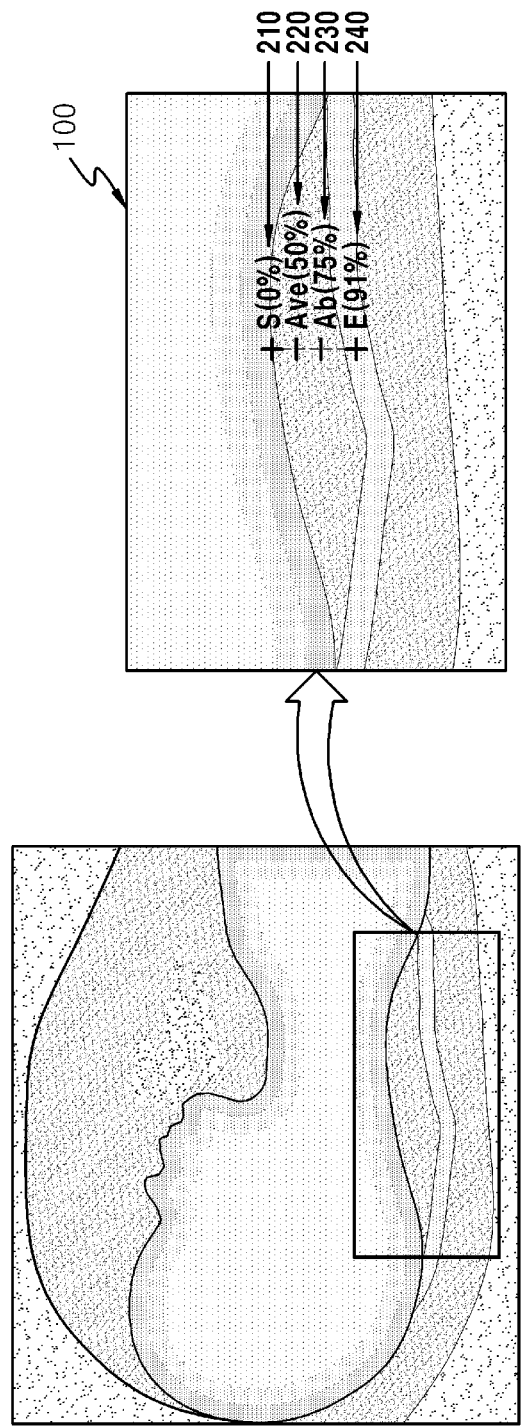
FIGS. 2A through 2E illustrate examples of displayed additional information related to a measured value of an object according to an exemplary embodiment of the present invention.

FIG. 2A illustrates the display of additional information related to a measured value of an object, according to an exemplary embodiment of the present invention. For example, if the object is a fetus, a user may measure a NT length (or thickness) of the fetus to determine the presence of fetal malformations. The malformations of a fetus being currently measured may be determined by using an average value of NT lengths of a plurality of fetuses having the same or similar GAs to that of the fetus being measured or a length (e.g., abnormal value) representing a high risk of malformations.

Upon designating (or clicking) a measurement start point S and a measurement end point E on a region of interest (ROI) 100 in an image of a fetus shown in FIG. 2, wherein the ROI includes a portion to be measured such as a nuchal portion, an NT length of the fetus corresponding to a length of a straight line between the measurement start and end points S and E may be measured. An average value Ave of NT lengths of a plurality of fetuses having the same or similar GAs to that of the fetus being measured may be determined. An abnormal value Ab that may also be defined as abnormal at a GA of the fetus being measured may be determined. As described above, the average value Ave, the abnormal value Ab, or a value of interest for diagnosis may be predetermined for a measurement item, or be determined using statistical operations while an object is being measured.

The operation of determining a reference value for a measurement based on acquired measurement item information according to an embodiment of the present invention may further include determining a percentile rank of an average value Ave, an abnormal value Ab, or a value of interest for diagnosis, which is related to a measured value of an object.

For example, a percentile rank of an average value Ave, an abnormal value Ab, or a value of interest for diagnosis may be determined based on measurement item information of the object. For example, percentile ranks of the average value Ave and the abnormal value Ab may be determined as 50% and 75%, respectively. The percentile ranks may be displayed as additional information related to the measured value, together with an image of the object.

Referring back to FIG. 2A, additional information 210 for the measurement start point S may be displayed. In other words, a percentile rank at the measurement start point S may be displayed as the additional information 210. Additional information 220 including a percentile rank of the average value Ave and additional information 230 including a percentile rank of the abnormal value Ab may also be displayed. Furthermore, additional information 240 including a percentile rank of a measurement end point E may be displayed. Since a length from the measurement start point S to the measurement end point E is greater than a length from the measurement start point S to the abnormal value Ab as shown in FIG. 2A, the user may determine that an NT length of the fetus currently being measured is abnormal.

Figure 2B:
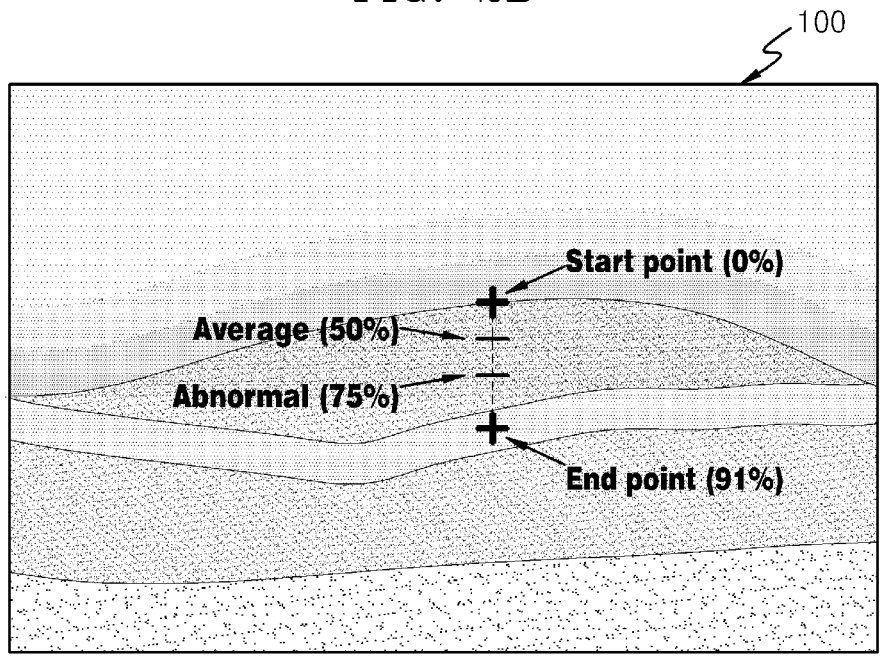

FIG. 2B illustrates another example of the display of additional information related to a measured value of an object.

As shown in FIG. 2, at least one of percentile ranks of a measurement start point, an average value, an abnormal value, and a measurement end point may be displayed as additional information. The additional information may be displayed in such a way as to overlap an image of the object in the form of a pop-up window or speech bubble.

Figure 2C:
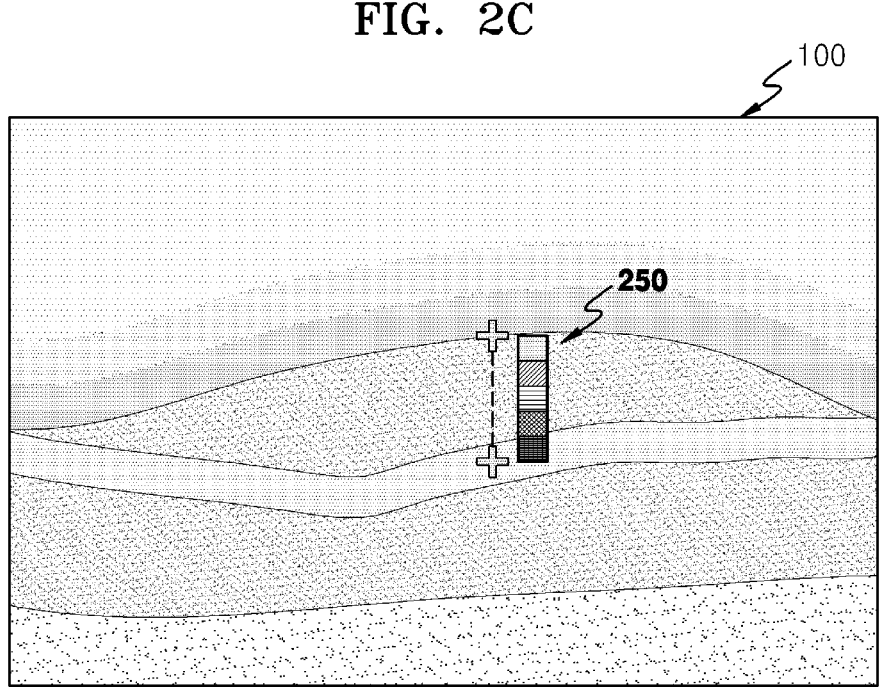

FIG. 2C illustrates another example of the display of additional information related to a measured value of an object.

A predetermined color may be assigned to an average value or an abnormal value determined based on measurement item information of the object. In this case, the gradation of colors may be assigned to respective values. For example, as a value changes from the average value to the abnormal value, the brightness or saturation of associated colors may increase. Blue, green and orange may be assigned to the measurement start point, the average value and the abnormal value, respectively. In other words, as the value changes from the measurement start point to the abnormal value, blue, green, yellow, orange, and red may be sequentially assigned to the respective values, but embodiments of the present invention are not limited thereto. For example, if a color bar having blue, green, yellow, orange, red arranged in this order may be provided as additional information, and if the measured value exceeds the abnormal value, the measured value corresponds to a location of a red interval in an image, and thus the user may determine the object as being abnormal.

Figure 2D:
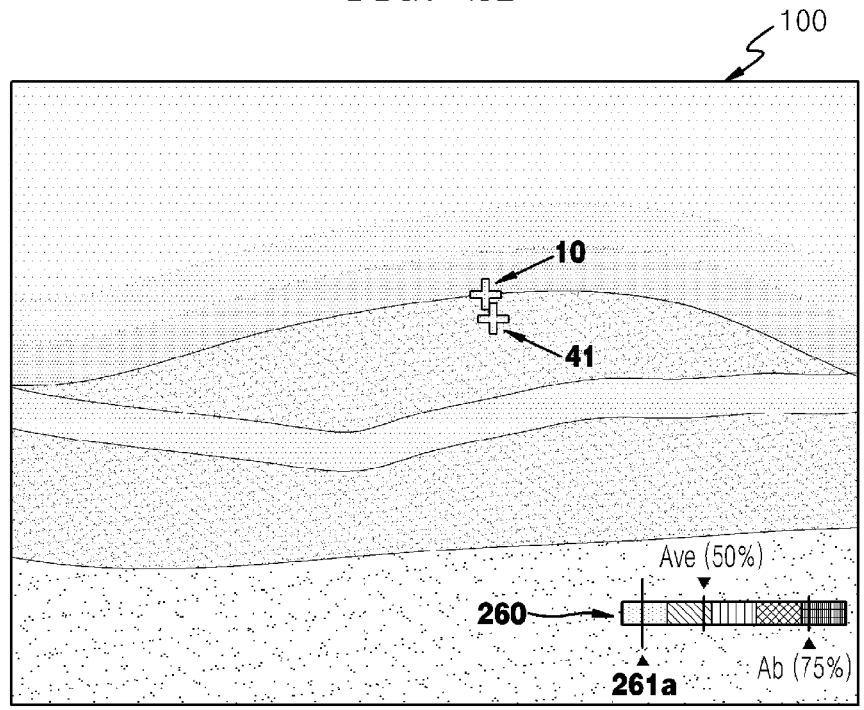

FIG. 2D illustrate an example of the display of a measured value of an object in colors.

Referring to FIG. 2D, a measurement start point 10 may be designated on an image of the object by using a predetermined pointer, and then a region of the object including a point designated by moving the pointer from the measurement start point 10 in a predetermined direction may be measured in real-time. In other words, a measured value of the object may be obtained in real-time as the pointer moves.

Furthermore, additional information 260 including an average value Ave, an abnormal value Ab, or a value of interest for diagnosis, which is related to the measured value, may be displayed together with the image of the object. A color bar as shown in FIG. 2C may also be displayed as additional information.

The measured value acquired in real-time may be displayed as a color assigned according to a range in which the measured value lies. For example, as shown in FIG. 2D, if the pointer is moved from the measurement start point 10 to designate a point 41 at a first location, a distance of a straight line between the measurement start point 10 and the point 41 at the first location falls within a blue interval 261a of the additional information 260, and thus the straight line therebetween may be displayed in blue.

Furthermore, if the pointer is moved from the measurement start point 10 to designate a point 42 at a second location, a distance of a straight line between the measurement start point 10 and the point 42 at the second location falls within a green interval 261b of the additional information 260, and thus the straight line therebetween may be displayed in green.

Similarly, if the pointer is moved from the measurement start point 10 to designate a point 43 at a third location, a distance of a straight line between the measurement start point 10 and the point 43 at the third location falls within an orange interval 261c of the additional information 260, and thus the straight line therebetween may be displayed in orange.

Since a measured value is displayed so as to correspond to displayed additional information when a user measures an object, the user may intuitively determine whether the object is normal or abnormal and easily identify a relative relationship between the measured value and the reference value by referring to the displayed additional information.

Figure 2E:
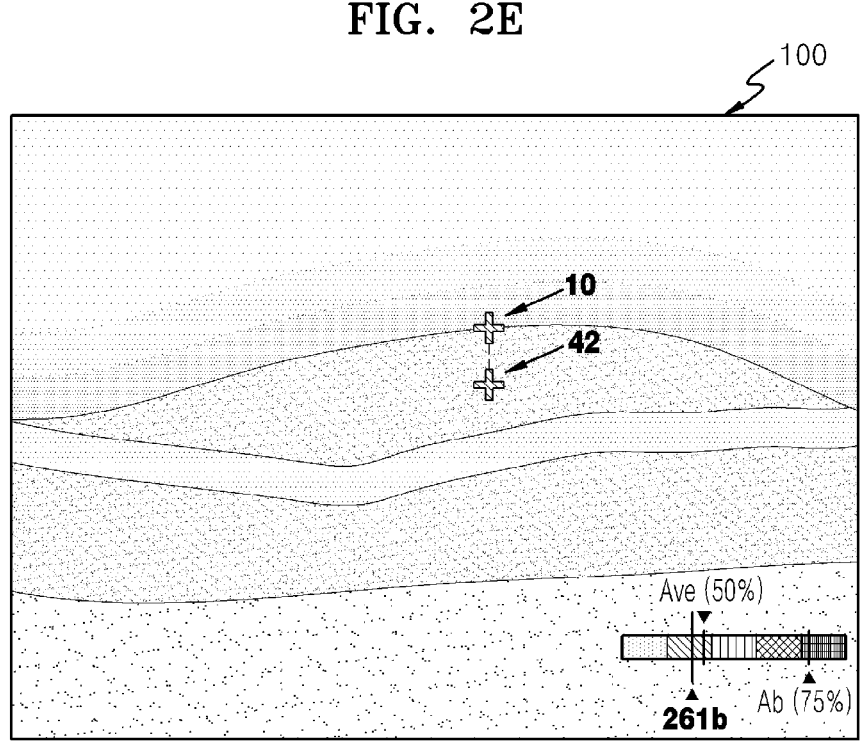

FIG. 2E illustrates another example of displayed additional information related to a measured value of an object.

Referring to FIG. 2E, a percentage of an abnormal value or measured value based on an average value may be displayed as additional information related to the measured value of the object. For example, if an average length from a measurement start point is set to 100%, the abnormal value and a measurement end point may be indicated as 125% and 213%, respectively, compared to the average value of 100%. In other words, the user is able to easily identify a relative relationship between the average value and the measured value or between the abnormal value and the measured value by referring to percentages of the abnormal value and the measured value based on the average value, which are displayed as additional information.

FIGS. 3A through 3D illustrate examples of displayed additional information related to a measured value of an object according to another exemplary embodiment of the present invention.

The measured value of the object may include a length, a perimeter, an angle, an area, or a volume.

Figure 3A:
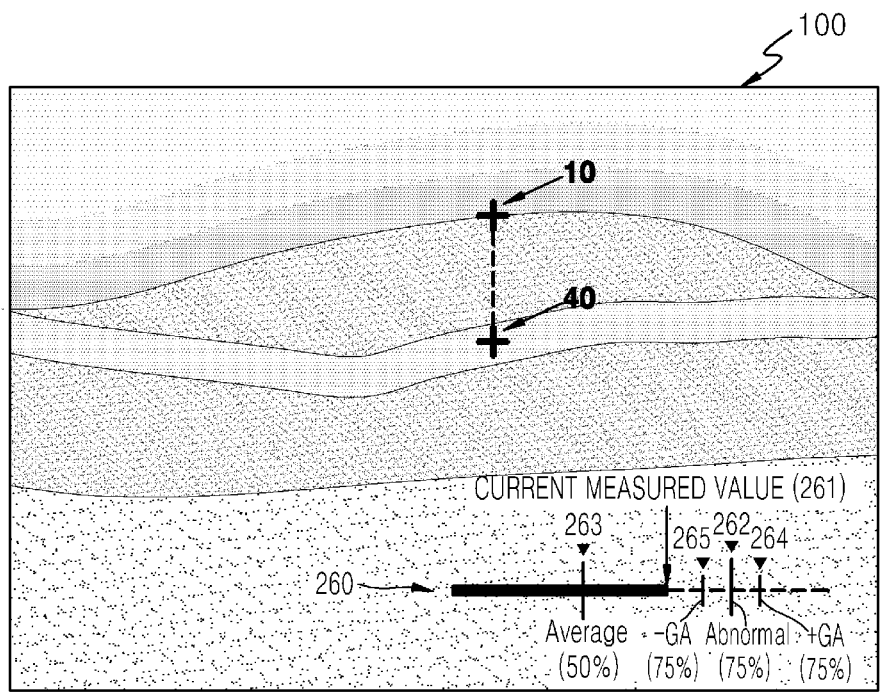
FIGS. 3A through 3D illustrate examples of displayed additional information related to a measured value of an object according to another exemplary embodiment of the present invention.

Referring to FIG. 3A, when a length of a portion of interest in an object is measured, additional information 260 including a current measured value 261 and a reference value such as an abnormal value 262 and an average value 263 may be displayed. For example, the current measured value 261 may be greater than the average value 263 but less than the abnormal value 262. The additional information 260 may further include an abnormal value 264 or 265 corresponding to a GA (for instance, −GA or +GA) predicted within an error range. The additional information 260 may further include an average value (not shown) corresponding to a GA predicted within the error range. The error range may be determined differently for each measurement item. For example, the error range may be one (1) week before a GA acquired as measurement item information or one (1) week after the GA.

Thus, by referring to the displayed additional information 260, the user may easily identify not only a difference between the current measured value 261 and either the average value 263 or the abnormal value 262 but also information about an average or abnormal value that falls within the error range, thus allowing accurate diagnosis of the object.

Figure 3B:
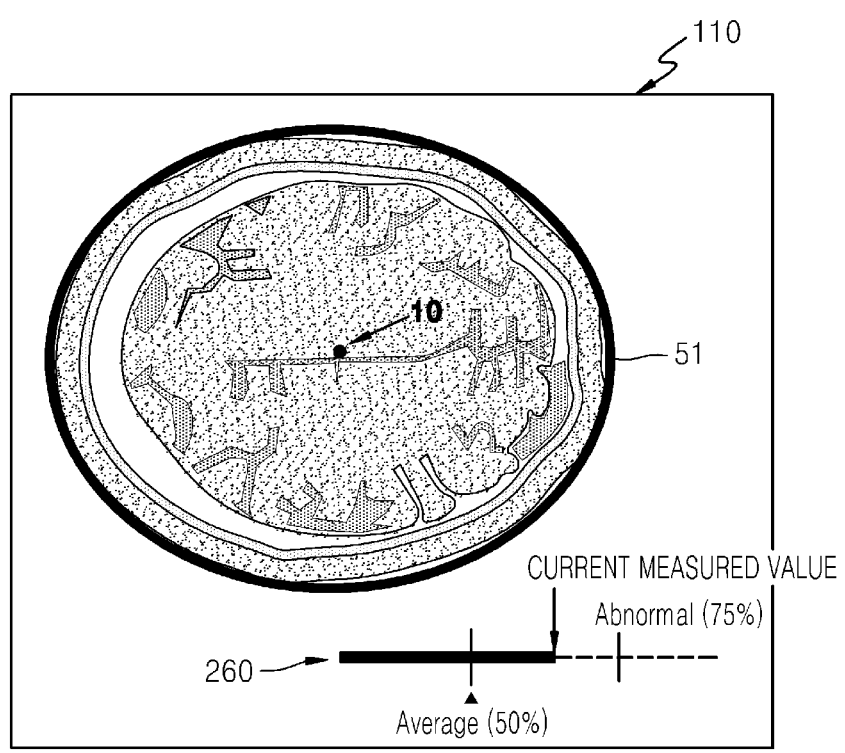

When an image 110 of an object shown in FIG. 3B is acquired, a user may measure a perimeter of a portion of interest in the object. For example, the user may measure a perimeter of a region that is separated from the measurement start point 10 by a distance equal to a radius. In this case, additional information 260 including the measured perimeter and a reference value such as an average value and an abnormal value may be displayed. The measured perimeter may be greater than the average value but less than the abnormal value.

Figure 3C:
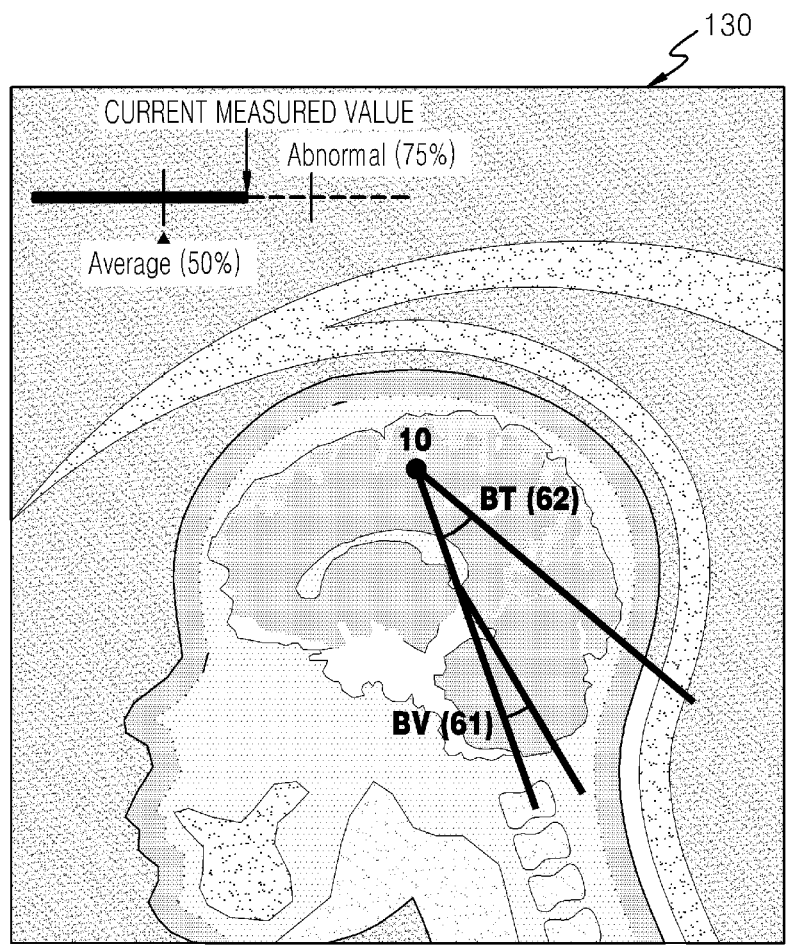

Furthermore, when an image 120 of an object shown in FIG. 3C is acquired, a user may measure an angle of a portion of interest in the object. For example, the user may measure a predetermined angle 61 or 62 formed with a straight line including a measurement start point 10. In this case, additional information 260 including the measured angle and a reference value such as an average value and an abnormal value may be displayed. As shown in FIG. 3C, the measured perimeter may be greater than the average value but less than the abnormal value.

Figure 3D:
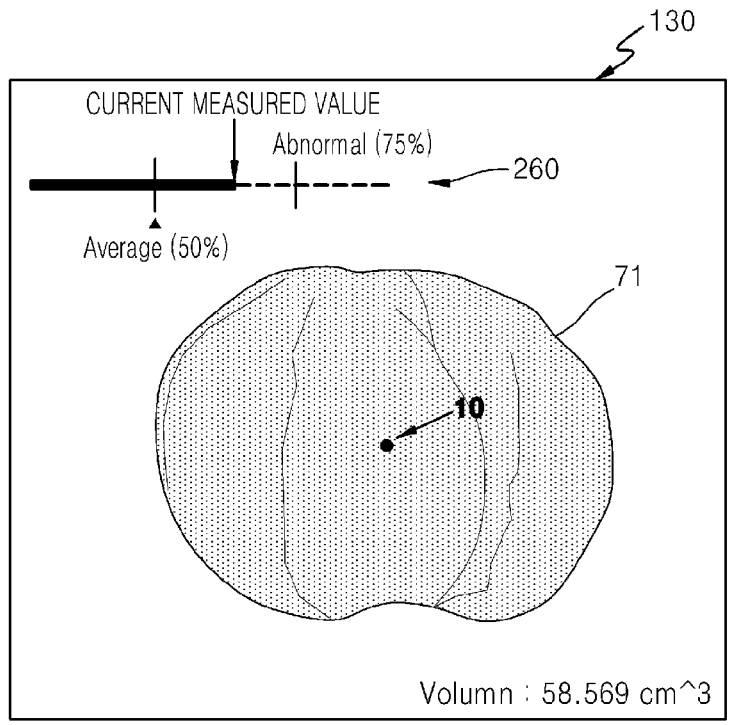

Furthermore, when a volume image 130 of an object shown in FIG. 3D is acquired, a user may measure a volume of a portion of interest in the object. For example, a volume of the portion of interest may be measured based on a measurement start point 10. In this case, additional information 260 including the measured volume and a reference value such as an average value and an abnormal value may be displayed. As shown in FIG. 3D, the measured volume may be greater than the average value but less than the abnormal value.

Although not shown in FIGS. 3B through 3D, as described above with reference to FIG. 3A, the additional information 260 may include an average value or an abnormal value corresponding to a GA and predicted within the error range.

Figure 4:
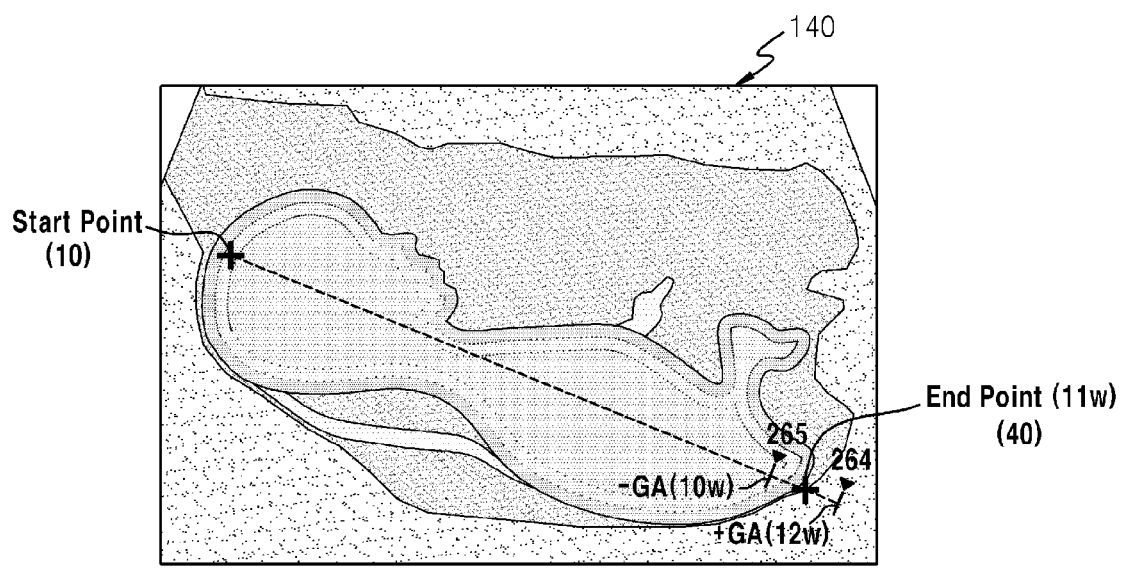
FIG. 4 illustrates additional information displayed together with a measured value of an object according to an exemplary embodiment of the present invention.

FIG. 4 illustrates additional information displayed together with a measured value of an object according to an exemplary embodiment of the present invention.

When an image 140 of an object shown in FIG. 4 is acquired, a user may measure a length or other dimensions of the object by designating a measurement start point 10 and a measurement end point 40. At the measurement end point 40, additional information associated with the measured value of the object may be displayed. For example, a GA of a fetus as the object may be predicted according to a value measured by using the measurement start and end points 10 and 40. If the predicted GA is 11 weeks, additional information 11W may be displayed at the measurement end point 40. Thus, the user may be provided with additional information related to a measured value upon measuring the object, thereby allowing fast diagnosis of the object.

The additional information may also include GAs 264 and 265 predicted within an error range. The error range may vary according to a measurement item. For example, the error range may be one week 265 before a GA predicted and displayed through measurement or one week 264 after the GA.

Figure 5:
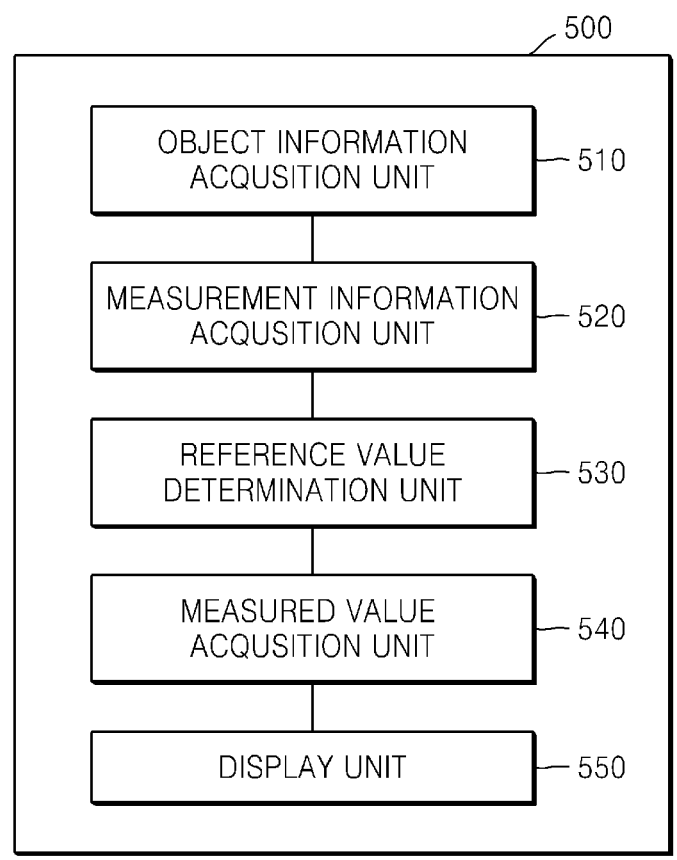
FIG. 5 is a block diagram of an apparatus for displaying additional information related to a measured value of an object, according to an exemplary embodiment of the present invention.

FIG. 5 is a block diagram of an apparatus 500 for displaying additional information related to a measured value of an object, according to an exemplary embodiment of the present invention.

Referring to FIG. 5, the apparatus 500 according to the present embodiment includes an object information acquisition unit 510 for acquiring measurement item information of an object, a measurement item information acquisition unit 520 for acquiring at least one of a measurement point and a measurement direction for the object, a reference determination unit 530 for determining a reference value for a measurement based on the acquired measurement item information, a measured value acquisition unit 540 for acquiring a measured value of the object based on at least one of the acquired measurement point and measurement direction, and a display unit 550 for displaying additional information including the determined reference value and the acquired measured value. The measurement item information of the object may include profile information of the object and information about measurement items that are determined according to a portion of the object to be measured.

The measurement point of the object may include a measurement start point and a measurement end point. The measurement end point may be designated by moving a predetermined pointer for designating the measurement point from the measurement start point in a predetermined direction. The predetermined pointer may include an arrow- or finger-shaped cursor.

The reference determination unit 530 may determine an average value or an abnormal value for a measurement item based on profile information of the object.

The measured value of the object may include a length, a perimeter, an angle, an area, or a volume. The measured value acquisition unit 540 may acquire a length of a straight line formed by moving a predetermined pointer from a measurement start point, a perimeter of a curve formed by moving the predetermined pointer from a measurement start point, an angle formed by a plurality of lines including a measurement start point, an area having a predetermined shape including a measurement start point, or a volume of a 3D region including a measurement start point.

The display unit 550 may display additional information including a reference value and a measured value at a predetermined location on a medical image of the object.

Figure 6:
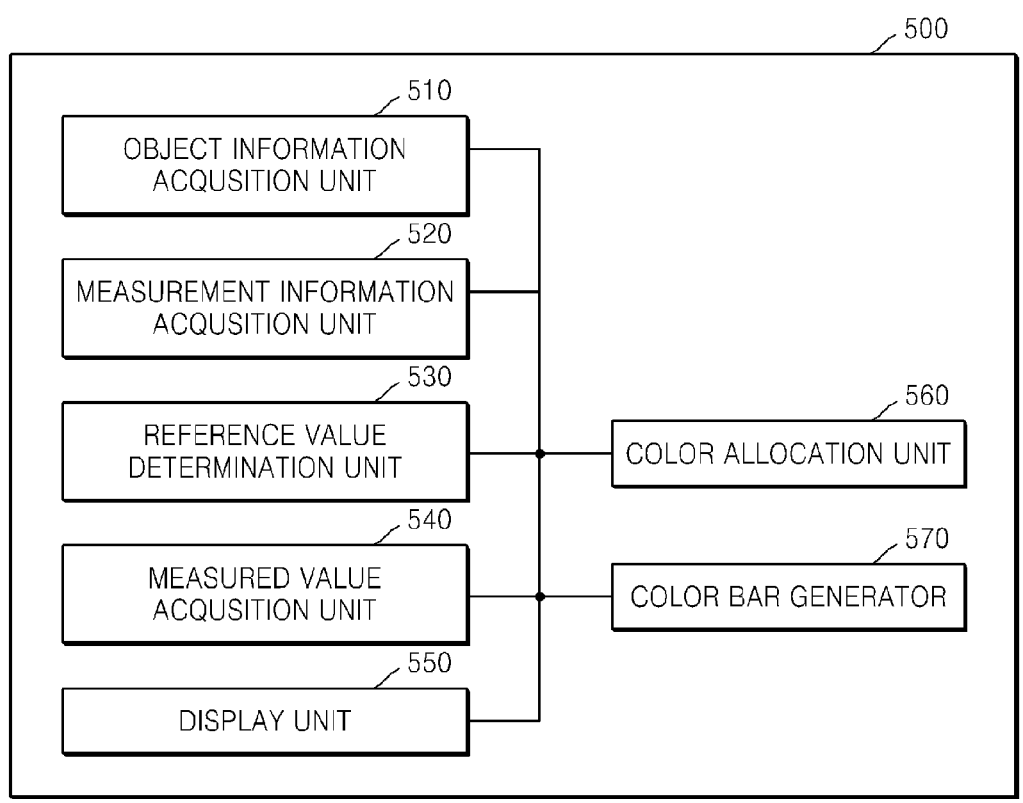
FIG. 6 is a block diagram of an apparatus for displaying additional information related to a measured value of an object, further including a color allocation unit and a color bar generator, according to another exemplary embodiment of the present invention.

FIG. 6 is a block diagram of an apparatus 500 for displaying additional information related to a measured value of an object, further including a color allocation unit 560 and a color bar generator 570 according to another exemplary embodiment of the present invention.

Referring to FIG. 6, the apparatus 500 according to the present embodiment may further include the color allocation unit 560 for allocating a predetermined color to a determined reference value and the color bar generator 570 for generating a color bar including a color allocated to the reference value.

A display unit 550 may display additional information including the reference value having the predetermined color and an acquired measured value at a predetermined location on a medical image of the object.

The predetermined location may overlap a straight line formed between measurement start and end points. In other words, the additional information may be displayed in such a way as to overlap the straight line therebetween.

The display unit 550 may also display the generated color bar as additional information. In this case, the predetermined location may be adjacent to a straight line formed between measurement start and end points A measured value acquisition unit 540 may acquire a measured value in real-time each time a predetermined pointer is moved from a measurement start point in a predetermined direction.

The display unit 550 may also display the generated color bar and the measured value in color that corresponds to a measured value obtained in real-time among colors included in the color bar.

Figure 7:
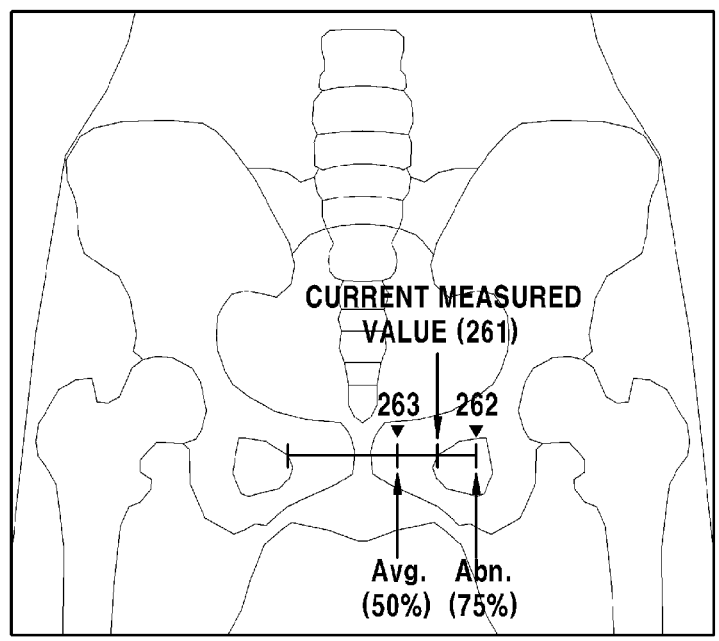
FIG. 7 illustrates displayed additional information related to a measured value of an object in an X-ray image, according to an exemplary embodiment of the present invention.
Figure 8:
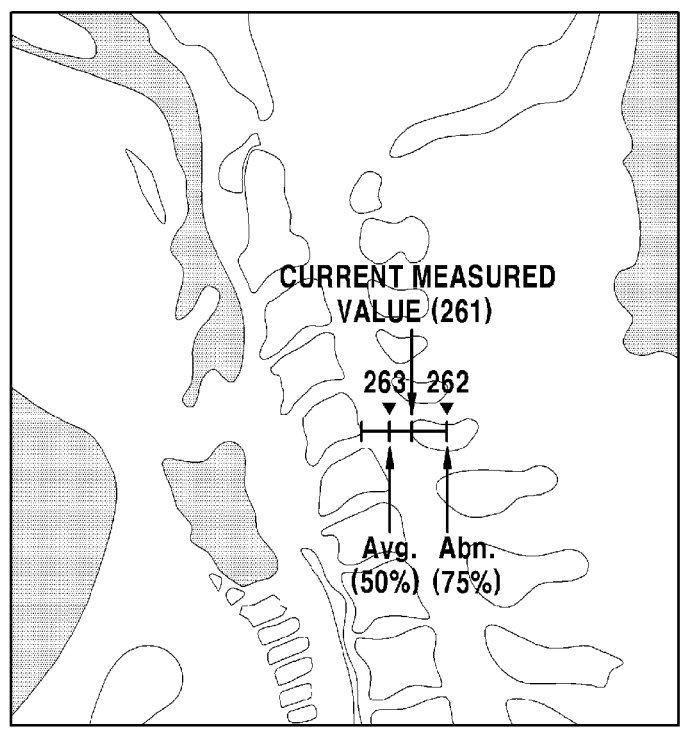
FIG. 8 illustrates displayed additional information related to a measured value of an object in a computerized tomography (CT) image, according to an exemplary embodiment of the present invention.
Figure 9:
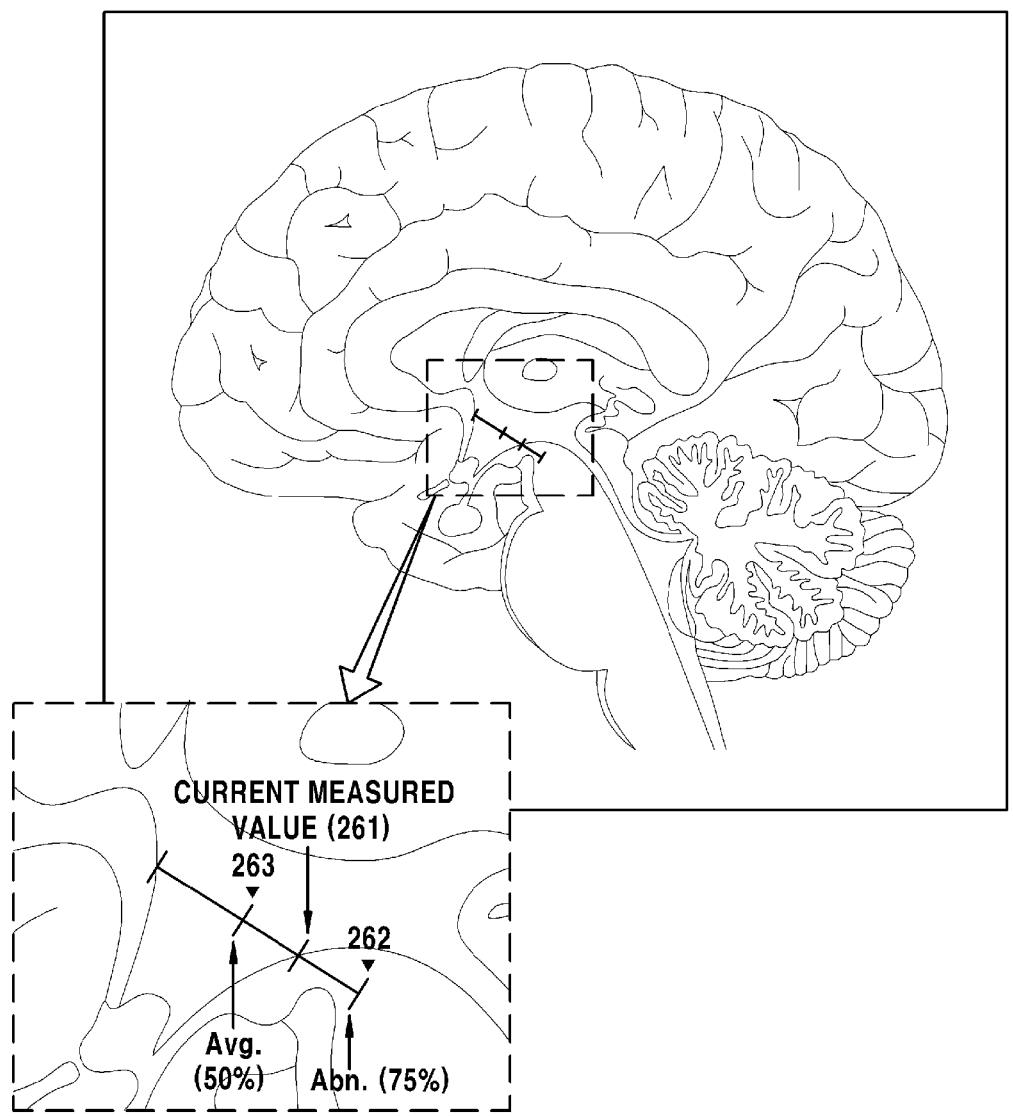
FIG. 9 illustrates displayed additional information related to a measured value of an object in a medical resonance imaging (MRI) image, according to an exemplary embodiment of the present invention.

FIG. 7 illustrates displayed additional information related to a measured value of an object in an X-ray image, according to an exemplary embodiment of the present invention. FIG. 8 illustrates displayed additional information related to a measured value of an object in a CT image, according to an exemplary embodiment of the present invention. FIG. 9 illustrates displayed additional information related to a measured value of an object in an MRI image according to an exemplary embodiment of the present invention.

As described above, a medical image may include ultrasound images as well as images of an object acquired by an X-ray, a CT, an MRI, and other medical imaging systems.

A user may identify the presence of abnormality of an object by measuring a length a portion of the object that the user desires to measure in an X-ray image of a pelvis of the object take using X-rays. For example, as shown in FIG. 7, an abnormal value 262 or an average value 263 may be displayed together with a current measured value 261 of the pelvis. Thus, the user may identify the presence of abnormality of the object based on the current measured value 261 by referring to the abnormal value 262 or the average value 263 provided as additional information. For example, the user may check for a status of an abnormal growth of a pelvis by measuring a length of the pelvis.

Furthermore, a user may identify the presence of abnormality of an object by measuring a width a portion of the object that the user desires to measure in a CT image of the object. For example, as shown in FIG. 8, an abnormal value 262 or an average value 263 may be displayed together with a current measured value 261 that is a width of a spine. Thus, the user may identify the presence of abnormality of the object based on the current measured value 261 by referring to the abnormal value 262 or the average value 263 provided as additional information. For example, the user may check for the presence of a cervical spinal canal stenosis by measuring a width of the spine.

Furthermore, a user may identify the presence of abnormality of an object by measuring a length a portion of the object that the user desires to measure in an MRI image of the object. For example, as shown in FIG. 9, an abnormal value 262 or an average value 263 may be displayed together with a current measured value 261 that is a length of a hypothalamus of a brain. Thus, the user may identify the presence of abnormality of the object based on the current measured value 261 by referring to the abnormal value 262 or the average value 263 provided as additional information. For example, the user may check the performance of a clinical function of a hypothalamus by measuring the length of hypothalamus.

Descriptions with respect to the apparatus may apply to descriptions of methods according one or more embodiments of the present invention. Thus, the same descriptions as already presented with respect to the apparatus are omitted in describing the method.

The embodiments of the present invention may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs), etc.

While one or more embodiments of the present invention have been described with reference to the figures, it will be understood by those of ordinary skill in the art that various changes in form and details may be made therein without departing from the spirit and scope of the present invention as defined by the following claims. Therefore, it should be understood that the exemplary embodiments described therein should be considered in a descriptive sense only and not for purposes of limitation. The scope of the invention is defined not by the detailed description of the invention but by the appended claims, and all differences within the scope of the appended claims and their equivalents will be construed as being included in the present invention.

What is claimed is:

1. A method of displaying additional information related to a measured value of an object, the method performed by a medical imaging system and comprising:
   acquiring measurement item information of the object;
   acquiring at least one of a measurement point and a measurement direction for the object;
   acquiring the measured value of the object based on the at least one of the measurement point and the measurement direction; and
   displaying additional information including a reference value predetermined for the measurement item information and the acquired measured value,
   wherein the measurement item information of the object comprises profile information of the object and information about a measurement item determined according to a portion of the object to be measured, and the reference value and the acquired measured value are displayed on a straight line.

2. The method of claim 1, wherein the measurement point comprises a measurement start point, and a measurement end point, which is designated by moving a pointer from the measurement start point in a direction for designating the measurement point.

3. The method of claim 1, wherein the reference value comprises at least one of an average value, an abnormal value, and a value of interest for diagnosis which are predetermined for the measurement item information.

4. The method of claim 2, wherein the measured value of the object comprises a length, a perimeter, an angle, an area, or a volume, and
   wherein the acquiring of the measured value of the object based on the at least one of the measurement point and the measurement direction comprises acquiring a length of a straight line formed by moving the pointer from the measurement start point, a perimeter of a curve formed by moving the pointer from the measurement start point, an angle formed by a plurality of lines including the measurement start point, an area of a shape including the measurement start point, or a volume of a 3D region including the measurement start point.

5. The method of claim 4, wherein the displaying of the additional information comprises:
allocating a predetermined color to the reference value; and
displaying the additional information including the reference value having the predetermined color and the measured value at a predetermined location on a medical image of the object.

6. The method of claim 5, wherein the predetermined location overlaps a straight line formed between the measurement start point and the measurement end point.

7. The method of claim 4, wherein the predetermined location is adjacent to a straight line formed between the measurement start point and the measurement end point, and
wherein the displaying of the additional information comprises:
allocating a predetermined color to the reference value;
generating a color bar including the color allocated to the reference value; and
displaying the generated color bar as the additional information.

8. The method of claim 4, wherein the measured value is acquired in real-time while the pointer is moved from the measurement start point in the direction, and the displaying of the additional information comprises:
allocating a predetermined color to the reference value;
generating a color bar including the color allocated to the reference value;
displaying the generated color bar; and
displaying the measured value in a color that corresponds to the measured value acquired in real-time among colors included in the color bar.

9. A medical imaging system for displaying additional information related to a measured value of an object, the system comprising:
a display; and
one or more processors configured to:
acquire measurement item information of the object;
acquire at least one of a measurement point and a measurement direction for the object;
acquire the measured value of the object based on the at least one of the measurement point and the measurement direction; and
control the display to display additional information including a reference value predetermined for the measurement item information and the acquired measured value,
wherein the measurement item information of the object comprises profile information of the object and information about a measurement item determined according to a portion of the object to be measured, and the reference value and the acquired measured value are displayed on a straight line.

10. The system of claim 9, wherein the measurement point comprises a measurement start point and a measurement end point which is designated by moving a pointer from the measurement start point in a direction for designating the measurement point.

11. The system of claim 9, wherein the reference value comprises at least one of an average value, an abnormal value, and a value of interest for diagnosis which are predetermined based on the measurement item.

12. The system of claim 10, wherein the measured value of the object comprises a length, a perimeter, an angle, an area, or a volume, and
wherein the processors configured to acquire a length of a straight line formed by moving the pointer from the measurement start point, a perimeter of a curve formed by moving the pointer from the measurement start point, an angle formed by a plurality of lines including the measurement start point, an area of a shape including the measurement start point, or a volume of a 3D region including the measurement start point.

13. The system of claim 12, wherein the processors are further configured to:
allocate a predetermined color to the reference value; and
control the display to display the additional information including the reference value having the predetermined color and the measured value at a predetermined location on a medical image of the object.

14. The system of claim 13, wherein the predetermined location overlaps a straight line formed between the measurement start point and the measurement end point.

15. The system of claim 12, wherein the predetermined location is adjacent to a straight line formed between the measurement start point and the measurement end point, and the processors further configured to:
allocate a predetermined color to the reference value;
generate a color bar including the color allocated to the reference value; and
control the display to display the generated color bar as the additional information.

16. The system of claim 12, wherein the measured value is acquired in real-time while the pointer is moved from the measurement start point in the direction, and the processors further configured to:
allocate a predetermined color to the reference value;
generate a color bar including the color allocated to the reference value; and
control the display to display the generated color bar, and the measured value in a color that corresponds to the measured value acquired in real-time among colors included in the color bar.

17. A non-transitory computer-readable recording medium having recorded thereon a program for executing the method of claim 1 on a computer.

* * * * *